(12) United States Patent
Zhong

(10) Patent No.: US 8,945,597 B2
(45) Date of Patent: Feb. 3, 2015

(54) BOTANICAL INSECTICIDES

(76) Inventor: Tao Zhong, North Bergen, MA (US)

( * ) Notice: Subject to any disclaimer, the term of this patent is extended or adjusted under 35 U.S.C. 154(b) by 0 days.

(21) Appl. No.: 13/526,455

(22) Filed: Jun. 18, 2012

(65) Prior Publication Data

US 2013/0336916 A1 Dec. 19, 2013

(51) Int. Cl.
| | | |
|---|---|---|
| *A01N 25/00* | (2006.01) | |
| *A01N 61/00* | (2006.01) | |
| *A01N 65/00* | (2009.01) | |
| *A01N 43/02* | (2006.01) | |
| *A01N 41/02* | (2006.01) | |
| *A01N 31/00* | (2006.01) | |
| *A01N 27/00* | (2006.01) | |

(52) U.S. Cl.
USPC .......... 424/405; 424/40; 424/84; 424/195.18; 424/747; 424/750; 424/754; 514/450; 514/517; 514/762; 514/729

(58) Field of Classification Search
CPC ..... A01N 25/04; A01N 25/006; A01N 25/32; A01N 27/00; A01N 31/04; A01N 37/14; A01N 41/02; A01N 43/04; A01N 65/06; A01N 65/22; A01N 65/42; A01N 65/44
USPC ............. 424/40, 84, 405, 406, 408, 409, 417, 424/195.18, 747, 750, 754; 514/450, 517, 514/762, 729

See application file for complete search history.

(56) References Cited

U.S. PATENT DOCUMENTS 6,004,569 A * 12/1999 Bessette et al. ............... 424/406
2013/0164361 A1 * 6/2013 Enan ............................ 424/405

* cited by examiner

*Primary Examiner* — Jeffrey T Palenik
(74) *Attorney, Agent, or Firm* — Milstein Zhang & Wu LLC

(57) ABSTRACT

The invention generally relates to environmental friendly pesticide compounds, formulations, methods of preparation and application and utilities thereof. More particularly, the invention relates to pesticide compounds and formulations that include terpenes or terpenoids having chemical formula of $(C_5H_8)_n$, and its derivatives and analogs thereof, as active insecticidal ingredients; certain botanical essential oils as synergists, and other select ingredients as additives.

10 Claims, No Drawings

BOTANICAL INSECTICIDES

TECHNICAL FIELD OF THE INVENTION

The invention generally relates to environmental friendly pesticide compounds, formulations, methods of preparation and application and utilities thereof. More particularly, the invention relates to pesticide compounds and formulations that include terpenes or terpenoids having chemical formula of $(C_5H_8)_n$, and its derivatives and analogs thereof, as active insecticidal ingredients; certain botanical essential oils as synergists, and other select ingredients as additives. The invention also relates method of manufacturing, various formulation and diverse utilities and applications including concentrated emulsion, powder, water-based spray and aerosol and useful for house hold, lawn, horticulture and agriculture in the purpose of control pest insect.

BACKGROUND OF THE INVENTION

Synthetic pesticide, which account for 70% of world pesticide market, dominates the global market of pest control products. Although synthetic pesticides have improved significantly in recent years on their chemical, environmental and toxicological properties, they continue to pose severe risks of harms to environment and human health due to their persistence and negative effects to non-target organisms. Synthetic pesticides unselectively attack nervous system components that are same in insects and vertebrates. Moreover, the extensive use of these synthetic materials creates tolerance and resistance in more and more pest insects, leading to continuously increase in the dosage of use and increased burden to the environment.

Terpens and terpenoids are important chemical compounds widely exist in plants, which have been found to exhibit insecticidal activities, providing resistance against phytophagous insect damage. For example, terpens and terpenoids exist typically in conifers, Rutaceae, Umbelliferae, Myrtaceae and Labiatae, Asteraceae, Lauraceae, Santalaceae, etc. They also exist in fungus. For example, sirenin can be extracted from Allomyces arbuscula, which resembles a lure to male insects. Terpens and terpenoids are also comprised of pheromones that are emitted from insect osmeterium. Terpenes and terpenoids are characterized by chemical structures of five-carbon isoprene units assembled and/or modified in various ways to form polymer chains or rings, which can be described as $(C_5H_8)_n$.

The mechanism of the toxic activities of terpenes and terpenoids is under research, although it is hypothesized that they act as allomones or they mimic insect pheromones representing semichemical communications between insect and plant. They are found to deliver in a vapor phase through penetration to target tissues via the respiration system of insects, which can result in antifeedant, repel, allure, growth inhibition, larvacidal, neuron toxication, etc.

Most terpenes and terpenoids that exhibit insecticidal activities are of the following three types: monoterpenes $(C_5H_8)_2$, sesquiterpenes $(C_5H_8)_3$ and diterpenoids $(C_5H_8)_4$.

Although some terpenes and terpenoids are main components of certain essential oils, not all of them are found in essential oils. Therefore, the type of essential oil should not be used to define different types of terpenes or terpenoids. Even for those terpenes and terpenoids that exist in essential oils, the same type of essential oil from different origins or different extraction methods can have different contents within. It is unpredictable based on an essential oil whether it contains a specific terpene or terpenoid and its abundance in the essential oil.

Several applications have been documented involving different types of essential oils or their blends in the purpose of killing or repelling insect pests. U.S. Pat. Nos. 6,114,384; 6,004,569; 6,342,536; 6,376,556 and 6,531,163 relate to a different type of chemicals that are characterized by a 6-carbon ring system which are not of terpenes or terpenoids.

U.S. Pat. No. 6,399,113 describes a lawn pesticide using extracts from cypress mixed with surfactant. However, since the cypress extracts usually contains more than 50 different phyto-chemical compounds and the application doesn't specify which chemical is the active ingredient, there is no way to define its insecticidal property quantitatively or its insecticidal mechanism.

US Patent Application 20030060379A1 describes an insecticidal soap, asserted to be an environmentally friendly pesticide. The disclosure compositions involve all commercially available botanical essential oils without specifying any specific compounds as active ingredients.

There continue to be an urgent need for environmental friendly pesticide compounds, formulations, methods of preparation and methods of using the same.

SUMMARY OF THE INVENTION

In one aspect, the invention generally relates to an insecticide composition having one or more environmentally safe terpenes or terpenoids as active ingredients, wherein each of the one or more terpenes or terpenoids has a structural formula of $(C_5H_8)_n$, wherein n is 2, 3 or 4.

In certain embodiments, each of the one or more terpenes and terpenoids is selected from the group consisting of 8-epicedrol, 1,8-cineole, allicin, ocimene, pinene, p-cymene, caryophyllene and menthol.

In some embodiments, the insecticide composition of the invention further includes one or more botanical essential oils or concretes as boosters.

In certain embodiments, the insecticide composition may further include one or more surfactants.

In some embodiments, the insecticide composition further includes one or more synergists.

The insecticide composition may be in various forms including concentrated emulsion, powder, water-based spray, aerosol, granule, powder, fumigation or lotion.

The insecticide composition may have insecticidal activities against Lepidoptera, Homoptera, Isoptera, Diptera, Orthoptera, hemiptera or Coleoptera.

In another aspect, the invention generally relates to a method for treating an insect infestation by applying an insecticide composition disclosed herein.

DETAILED DESCRIPTION OF THE INVENTION

The invention is based in part on the discovery of unique formulations of insecticidal (i.e., pesticide) compounds, which are environmentally safe to use. Such compounds and formulations include terpenes or terpenoids having chemical formula of $(C_5H_8)_n$, and its derivatives and analogs thereof, as active pesticidal ingredients; certain botanical essential oils as synergists, and other select ingredients as additives. The invention also relates method of manufacturing, various formulation and diverse utilities and applications including concentrated emulsion, powder, water-based spray and aerosol and useful for house hold, lawn, horticulture and agriculture in the purpose of control pest insect.

One primary objective of the present invention is to provide an environmentally safe pesticide that kills and repels pest insects, especially infraclasses of neoptera, including but not limited to, lepidoptera, homoptera, isoptera, diptera, orthoptera, hemiptera and coleoptera, of home, garden, livestock and agriculture, and at the same time used as sterilization and fungicide.

Another objective of the present invention is to provide an environmentally safe pesticide that uses one or more terpenes or terpenoids compounds extracted from botanical material as the active ingredients, which are characterized by structure of $(C_5H_8)_n$ and its derivatives.

Yet another objective of the present invention is to provide an environmentally safe pesticide that only repels or kills pest insects, e.g., at contact, but does no harm to human, animal, fish and bird.

Yet another objective of the present invention is to provide an environmentally safe pesticide that is bio-degradable and leaves no harmful residue to the soil and water.

It is also another objective of the present invention to provide an environmentally safe pesticide that includes one or more terpenes or terpenoids compound, one of multiple botanical essential oil or botanical concretes as synergists and other select additives, whereas the combined insecticidal efficacy is enhanced.

It is yet another objective of the present invention is to provide a formulation of an environmentally safe pesticide and the method of manufacturing same. The formulation can be made into many different forms, including but not limited to, concentrated emulsion, powder, water-based spray and aerosol.

To achieve the objective of the present invention, the environmentally safe botanical pesticide of the invention includes one or more botanical distillation extracts, more specifically certain terpenes or terpenoids that has structure of $(C_5H_8)_n$ and its derivatives, To achieve the objective of the present invention, the environmentally safe botanical pesticide of the invention also includes one or more botanical essential oils or botanical concretes as booster.

To achieve the objective of the present invention, the said environmental friendly botanical pesticide of the invention also may include one or more surfactants and/or synergists that are of food and cosmetic grade and biodegradable.

In one aspect, the invention generally relates to an insecticide composition having one or more environmentally safe terpenes or terpenoids as active ingredients, wherein each of the one or more terpenes or terpenoids has a structural formula of $(C_5H_8)_n$, wherein n is an integer from 2 to 4. The insecticide composition may include one, tow, three or multiple, or more environmentally safe terpenes or terpenoids as active ingredients, wherein each of the one or more terpenes or terpenoids has a structural formula of $(C_5H_8)_n$.

In certain embodiments, each of the one or more terpenes and terpenoids is selected from the group consisting of 8-epicedrol, 1,8-cineole, allicin, ocimene, pinene, p-cymene, caryophyllene and menthol.

In some embodiments, the insecticide composition of the invention further includes one or more botanical essential oils or concretes as boosters. Exemplary botanical essential oils or concretes are camphor oil, litsea cubeba oil, spearmind oil, citronella oil, cassia oil, star anise oil, cedar wood oil, peppermint oil, wintergreen oil and orris concrete.

In certain embodiments, the insecticide composition may further include one or more surfactants. Exemplary surfactants include ethanolamine dodecyl sulfate (K12 EA), sodium dodecyl sulfate (AS), potassium dodecyl phosphate(PK), linear sodium alkyl benzene sulfonate (LAS), sodium oleoyl amino fatty acid, sodium N-oleoyl-N-methyl taurinate, sodium salt α-sulfo fatty acid methyl ester (MES), sodium stearate, sodium oleate, ammonium oleate, potassium oleate, potassium stearate, zinc stearate, magnesium stearate, polyoxyethylene fatty alcohol sodium sulfate (AES), ethoxylated alkyl ester sulfo succinate, alkylbenzene sulfonic acid, sodium alkyl sulfonate, α-alkene-sulfonate (AOS), secondary alkane sulfonate (SAS), sodium dialkyl ester sulfonsuccinate, N-acyl glutamate (AGA), triethanolamine polyoxyethylene fatty alcohol sulfate (TA-40), sulfonated caster oil, Span-20, 40, 60, 65, 80, Tween-20, 40, 60, 65, 80, secondary alcohol polyoxyethylene ether (JFC), fatty alcohol polyoxyethylene(3) ether (AEO3), fatty alcohol polyethoxylate(7) ether (AEO7), fatty alcohol polyoxyethylene(9) ether (AEO9), fatty alcohol polyethoxylate(10) ether (AEO10), fatty alcohol Polyoxyethylene(15) ether (AEO15), fatty acid alkanol amide, fatty acid polyoxyethylene(10) ester, glyceryl oleate, glycerol trioleate, glyceryl stearate, alkylphenol polyoxyethylene(10) ether, coco fatty diethanol amide, coco fatty monoethanol amide, caster oil polyoxyethylene ether, ethoxylated metluyl glucoside sesquistearate (MSE), methyl glucoside sesquistearate, sucrose fatty acid ester, polyoxyethylene-polyoxypropylene glycols, polyoxyethylene alkylamide, dodecyl dimethyl betaine, alkyl dimethyl betaine, coco amino propyl betaine, carboxylate-type imidazoline ampholytic surfactant, carbomer, ethoxylated lanoilu, ethoxylated lanoilu alcohol, lanolin fatty acid, iso-propyl lanolate, liquid lanolin, and lecithin.

In some embodiments, the insecticide composition further includes one or more synergists. Exemplary synergists include alkyl glucoside, lactic acid, methyl silicone oil, isopropyl alcohol, ethanol, oleic acid, polyoxyethylene alkyl ether, alkyl sulfates, dialkyl succinate, alkyl amide taurine salt, fatty alcohol polyoxyethylene ether sulfonate, fatty alcohol ethoxylates, lactic acid ethyl ester, phenethyl propionate, polyglyceryl stearate, sodium polyacrylate, calcium lignin sulfonate, dialkyl succinate sulfonate, ethylene glycol monoether, amyl acetate, 2-butanone, n-butyl alcohol, dibutyl phthalate and n-butyl acetate.

The insecticide composition may be in various forms including concentrated emulsion, powder, water-based spray, aerosol, granule, powder, fumigation or lotion.

The insecticide composition may have insecticidal activities against lepidoptera, homoptera, isoptera, diptera, orthoptera, hemiptera or coleoptera.

In another aspect, the invention generally relates to a method for treating an insect infestation by applying an insecticide composition disclosed herein.

For example, certain embodiments of the environmentally safe botanical pesticide include:
One or more terpenes or terpenoids 0.5-70%
One or more essential oil or botanical concretes 0%-30%
One or more auxiliaries 0.1-50%, and
Water 5-90%

The broad range of concentration with water reflects that the insecticide compositions of the present invention have good water solubilities, they can either be a concentration with minimum water content, or it can be diluted in water at a desired concentration.

In some embodiments, the present invention provides a formula with weight content as below:
One or more terpenes or terpenoids: 5-70%
One or more essential oil booster: 1% -30%
One or more surfactants: 10%-30%
One or more synergists: 1%-10%
Water 5-20%

Not all terpenes or terpenoids present insecticidal activity. Some may act as lures to pest insects.

Exemplary compounds listed here have been tested and proved to present significant insecticidal properties and thus can be used as active ingredients in the present invention: 8-epicedrol, 1,8-cineole, allicin, ocimene, pinene, p-cymene, β-caryophyllene and 3-p-menthanol. The chemical structures are as shown below:

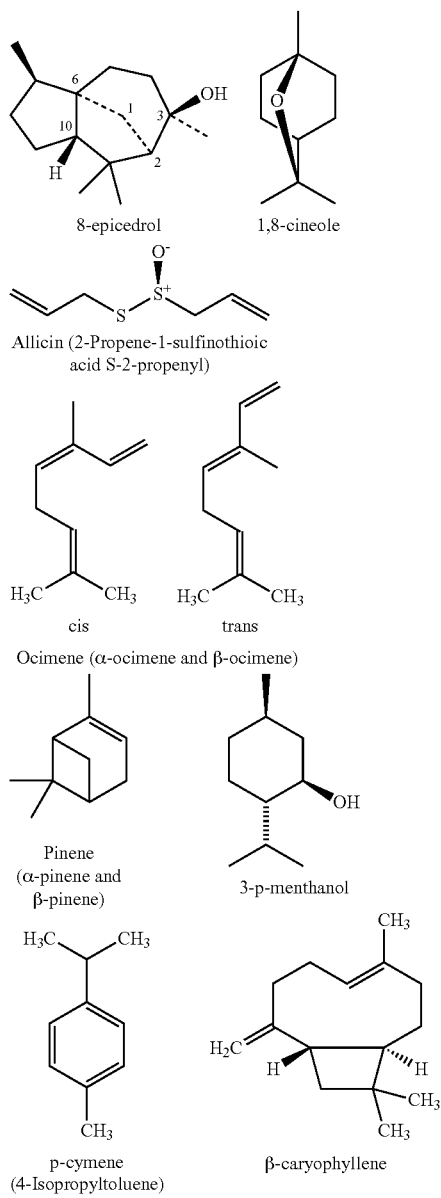

The above phyto-chemical compounds can be extracted from various parts of plants, e.g., by distillation or refinery of products of essential oils of which a desired compound is a component. For example, 8-epicedrol can be extracted from pine wood; 1,8-cineole can be extracted from eucalyptus leaves; allicin can be extracted from garlic; ocimene can be extracted from basil leaves; pinene exists in many different pine or cedar wood; geraniol can be extracted from geranium; and p-cymene can be extracted from ledum latifolia, caryophyllene from Dianthus and menthol from peppermint leaves.

Although some of these compounds can be obtained from refinery distillation of essential oils, directly using essential oils is not recommended. Essential oils are natural plant by-products and each type of oil contains 60 or more different compounds. The composition can be varied by many factors: species, different parts of the plant, geographical origins, etc. Even in the same plant the composition can vary, as a result of the physiological development of the plant, and its degree of maturity, climate, soil conditions, or even the method of extraction. To achieve a qualitative and quantitative control of the insecticidal activity, specific extraction practice should be followed to obtain desired compound.

Some essential oils or botanical concretes can be used as boosters to enhance the insecticidal activity of the main insecticide ingredients. Examples of such essential oils include camphor oil, litsea cubeba oil, spearmind oil, citronella oil, cassia oil, star anise oil, cedar wood oil, peppermint oil, wintergreen oil and orris concrete.

Several extraction methods for terpenes and terpenoids are commonly used: distillation, solvent extraction or alkaline acid precipitation, then followed by re-crystallization and chromatography separation and purification. For example, the method employed in the present invention is steam distillation and chromatography separation. Desired terpenes or terpenoids are then fractionated at a specific temperature due to terpenes and terpenoids' higher boiling points comparing to other components in essential oils. Distillation and fractionation procedure are as below:

1) Botanical raw material is chopped and grinded, and then made wet with water;
2) Steam goes through material and crude oil is distillated through condenser;
3) Crude essential oil is refined using salt precipitation and solvent extraction to obtain refined oil; and
4) Refined oil is further distilled and desired terpenes and/or terpenoids are fractionated at specific temperatures.

Some of the pure terpenes or terpenoids are in crystalline form at room temperature, such as menthol and 8-epicedrol. In such cases, refined oil can be used after fractionation to ensure a desired content of these phyto-chemical compounds. To guarantee a certain content of a desired terpenes or terpenoids, quantitative analysis is preferred such as MS and HPLC.

Surfactant can be Selected from Below Group:

Ethanolamine dodecyl sulfate (K12 EA), sodium dodecyl sulfate (AS), potassium dodecyl phosphate(PK), linear sodium alkyl benzene sulfonate (LAS), sodium oleoyl amino fatty acid, sodium N-oleoyl-N-methyl taurinate, sodium salt of α-sulfo fatty acid methyl ester (MES), sodium stearate, sodium oleate, ammonium oleate, potassium oleate, potassium stearate, zinc stearate, magnesium stearate, polyoxyethylene fatty alcohol sodium sulfate (AES), ethoxylated alkyl ester sulfo succinate, alkylbenzene sulfonic acid, sodium alkyl sulfonate, α-alkene-sulfonate (AOS), secondary alkane sulfonate (SAS), sodium dialkyl ester sulfonsuccinate, N-acyl glutamate (AGA), triethanolamine polyoxyethylene fatty alcohol sulfate (TA-40), sulfonated caster oil, Span-20, 40, 60,65,80, Tween-20, 40, 60, 65, 80, secondary alcohol polyoxyethylene ether (JFC), fatty alcohol polyoxyethylene (3) ether (AEO3), fatty alcohol polyethoxylate(7) ether (AEO7), fatty alcohol polyoxyethylene(9) ether (AEO9), fatty alcohol polyethoxylate(10) ether (AEO10), fatty alcohol Polyoxyethylene(15) ether (AEO15), fatty acid alkanol amide, fatty acid polyoxyethylene(10) ester, glyceryl oleate, glycerol trioleate, glyceryl stearate, alkylphenol polyoxyethylene(10) ether, coco fatty diethanol amide, coco fatty monoethanol amide, caster oil polyoxyethylene ether, ethoxylated metluyl glucoside sesquistearate (MSE), methyl glucoside sesquistearate, sucrose fatty acid ester, polyoxyethylene-polyoxypropylene glycols, polyoxyethylene alkylamide, dodecyl dimethyl betaine, alkyl dimethyl betaine, coco amino propyl betaine, carboxylate-type imidazoline ampholytic surfactant, carbomer, ethoxylated lanoilu, ethoxylated lanoilu alcohol, lanolin fatty acid, iso-propyl lanolate, liquid lanolin, and lecithin, Synergists can be Selected from Below Group:

Alkyl glucoside, lactic acid, methyl silicone oil, isopropyl alcohol, ethyl lactate, ethanol, oleic acid, polyoxyethylene alkyl ether, alkyl sulfates, dialkyl succinate, alkyl amide taurine salt, fatty alcohol polyoxyethylene ether sulfonate, fatty alcohol ethoxylates, lactic acid ethyl ester, phenethyl propionate, polyglyceryl stearate, sodium polyacrylate, calcium lignin sulfonate, dialkyl succinate sulfonate, ethylene glycol monoether, amyl acetate, 2-butanone, n-butyl alcohol, and dibutyl phthalate and n-butyl acetate.

Advantages of the insecticide compositions of the invention include that evenness of dispersed system when the material is diluted with water, and the high effectiveness in penetration, spreading and with slow releasing capability providing longer residue efficacy.

In certain preferred embodiment (1), the present invention provides a formula as below:

8-epicedrol 0.1-80%
Amyl acetate 0%-5%
Lethecin 0.5%-15%
Alkyl glucoside 0.5%-10%
Polyoxyethylene alkyl ether 0.5%-10%
Water 1% -10%

In certain other preferred embodiment (2), the present invention provides a formula as below:

Menthol 0.1-80%
litsea cubeba oil 0.1%-20%
isopropyl alcohol 0%-5%
Lethecin 0.5%-15%
Alkyl glucoside 0.5%-10%
Polyoxyethylene alkyl ether 0.5%-10%
Water 1% -10%

Other exemplary embodiments of the present invention includes the followings:

p-cymene 1-5%
Wintergreen oil 0.5-2%
Peppermint oil 0.5-2%
sodium dodecyl sulfate 10-20%
Span-20 10-20%
phenethyl propionate 5-10%
water 51-73%
8-epicedrol 30-50%
Cedar wood oil 5-10%
Peppermint oil 5-10%
Cassia oil 1-5%
Glyceryl monooleate 10-15%
Potassium stearate 2-8%
methyl silicone oil 1-5%
water 2- 46%
allicin 10-20%
Litsea cubeba oil 2-5%
Spearmind oil, 2-5%
fatty acid alkanol amide 10-15%
caster oil polyoxyethylene ether 3-20%
glycerol trioleate 1-5%
dialkyl succinate 1-5%
water 25-71%
1,8-cineole 15-20%
Citronella oil 5-10%
potassium oleate 10-15%
Glyceryl dioleate 6-12% lactic acid ethyl ester 3-5%
water 38- 61%
ocimene 18-25%
Star anise oil 5-12%
Ethanolamine dodecyl sulfate (K12 EA) 16-22%
linear sodium alkyl benzene sulfonate (LAS) 5-12%
sodium alkyl sulfonate 3-7%
phenethyl propionate 2-8%
water 14- 51%
pinene 20-30%
Cedar wood oil 5-20%
secondary alcohol polyoxyethylene ether (JFC) 6-20%
linear sodium alkyl benzene sulfonate (LAS) 3-10%
Ethylene glycol monoether 2-6%
methyl silicone oil 3-10%
water 4%-61%
p-cymene 1-10%
caryophyllene 0.5-4%
ethoxylated metluyl glucoside sesquistearate (MSE) 0.2-5%
Tween-60 0.2-5%
fatty alcohol Polyoxyethylene(15) ether (AEO15) 0.1-3%
dibutyl phthalate 0.1-3%
water 70-97.9%
1,8-cineole 25-35%
coco fatty diethanol amide 10-15%
dodecyl dimethyl betaine 4-10%
lecithin 3-8%
fatty alcohol ethoxylates 2-6%
water 36-55%
menthol. 20-30%
fatty alcohol polyethoxylate(7) ether (AEO7) 4-12%
dodecyl dimethyl betaine 2-8%
glycerol trioleate 3-10%
alkyl sulfates 1-6%
water 34-70%

The procedure for preparation is as below: dissolve all the surfactants and synergists in water to make inerts mixture, and agitate with homogenizer until the solution gets transparent. Prepare mixture of Menthol, litsea cubeba oil and mix completely. Adding active ingredients mixture into the additive mixture, heat to 60° C. and homogenize completely to make emulsion concentrate.

For application at home, garden and on agriculture, simply dilute the emulsion concentrate in water by ratio of 1:10 to 1:1000, and spray with bottle or hose.

Based on the above preferred embodiment, the present invention also provides further formula for different forms including but not limited to spray, granule, powder, fumigation, lotion.

To prepare for spray, simply dilute above mentioned preferred embodiment in water in a ratio 1:10 to 1:1000, or resolve selected terpenes and terpenoids in solvent such as ethanol or isopropyl alcohol in the weight content as below:

Selected terpenes or terpenoids: 0.5%-50%

Solvent: 50%-99.5%

To prepare for granulation, filling and releasing agent such as β-cyclodextrin, or sodium alginate or carboxymethylcellulose, are also used. Method includes mixing above mentioned preferred embodiment with β-cyclodextrin, or sodium alginate or carboxymethylcellulose, and stir at 10~100° C., 500~2000 r/min for 5-20 minutes, then dried and granulated.

To prepare for lotion, thickener may be used such as carbomer, bee wax, glyceryl stearate, lanolin alcohol, sorbitol or xanthan gum during the mixing process.

The present invention can also be mixed with other conventional pesticides in the forms including but not limited to emulsion concentrate, suspension concentrate, emulsion in water, wettable powder, dry powder, etc.

EXAMPLES

Examples 1

Insecticidal Efficacy Test Against Aphid Nymphs (*Aphis medicagini*)

Take the first preferred embodiment, diluted in water in two different concentrations, A with 1% weight content of active ingredients, B with 0.1% active ingredients. Vicia leaf cut into round disc in 2 cm diameter, back up placed on a small cotton ball, and then mounted in a Petri dish, 5 ml water is added. Mature aphids are transferred onto the leaf disc to hatch aphid nymphs. Mature aphids are removed after 24 hours and 20-30 aphid nymphs are left on the leave disc and continue to culture for one day. The leave disc with aphid nymphs is merged into solution A and B for 5 seconds, excessive fluid on the leaf surface is absorbed by paper tower. Leaf disc is then mounted back to the cotton ball for another 24 hours observation. Use Nitenpyram 20 mg/L for comparison and water as control. Mortality rate after 24 hours as below:

TABLE 1

| TEST CHEMICAL | TARGET INSECT | CONCENTRATION | MOTALITY % |
|---|---|---|---|
| EMBODIMENT 1 | *Aphis medicagini* | 1% | 100 |
| | | 0.1% | 90 |
| Nitenpyram | | 20 mg/L | 100 |
| CONTROL | | N/A | 0 |

The result indicates that at a concentration 0.1%, the Embodiment 1 has an equivalent insecticidal efficacy towards aphid nymphs comparing to nitenpyram which is a synthetic pesticide.

Example 2

Insecticidal efficacy test against planthopper nymphs (*nilaparvata legen*). Some rice seedling leaves are mounted with white quartz sand in a Petri dish with 5 cm diameter containing 5 ml water. Planthoppers nymphs of mid 3rd instar were anesthetized by $CO_2$. 20-30 anesthetized nymphs are transferred to each Petri dish and placed under the POTTER sprayer. Same amount of testing chemical is sprayed into each Petri dish and covered with transparent plastic cup. Use nitenpyram 20 mg/L for comparison and water as control. Mortality rate after 72 hours as below:

TABLE 2

| TEST CHEMICAL | TARGET INSECT | CONCENTRATION | MOTALITY % |
|---|---|---|---|
| EMBODIMENT 2 | *Nilaparvata legen* | 1% | 100 |
| | | 0.1% | 95 |
| Nitenpyram | | 20 mg/L | 100 |
| CONTROL | | N/A | 0 |

The result indicates that at a concentration 0.1%, the Embodiment 2 has an equivalent insecticidal efficacy towards planthopper nymphs comparing to Nitenpyram which is a synthetic pesticide.

Example 3

Insecticidal Efficacy Test Against Mosquito Nymphs

Take embodiment 2 and dilute to 5% solution. Take 6 beakers of 50 ml. In each of beaker, 45 ml deionized water is added first. 10 mosquito nymphs of 4th instar were transferred into each beaker and deionized water is added to total 50 ml. Take another 6 beakers of 250 ml, 0.1 ml, 0.2 ml, 0.5 ml, 1 ml and 2 ml of 5% Embodiment 2 is added into each beaker respectively, deionized water is added in each one to 150 ml, then and mixed completely. Transfer 50 ml water containing mosquito nymphs into each of 5 solutions. Use another beaker containing 200 ml deionized water as control. Mortality is observed after 24 hours. Each concentration is repeated for 3 times, average mortality rate is calculated.

TABLE 3

| TEST CHEMICAL | TARGET INSECT | CONCENTRATION | MOTALITY % |
|---|---|---|---|
| EMBODIMENT 2 | Mosquito nymphs | 0.025% | 0 |
| | | 0.05% | 40 |
| | | 0.125% | 76.7 |
| | | 0.25% | 100 |
| | | 0.5% | 100 |
| CONTROL | | N/A | 0 |

The result indicates that starting with concentration 0.125% the Embodiment 2 shows noticeable insecticidal activity towards mosquito nymphs.

Example 4

Fungicidal Efficacy test Against *Botrytis cinerea*

Two potted cucumber seedlings with similar true leaf stage are selected. Diluted Embodiment 1 is sprayed on to the leaves and let dry. Bacteria culture disc is inoculated to the leaves and maintain at temperature 24-26° C. under moisture condition. Pot is kept in dark for 24 hours and then in nature light for another 4 days. After onset of the infection on the control, infected area is measured with caliper and infection control index is calculated.

Infection control index (%)=(infected area on control−infected area on treatment)×100/infected area on control

TABLE 4

| TEST CHEMICAL | CONCENTRATION mg/L | *Botrytis cinerea* CONTROL INDEX % |
|---|---|---|
| EMBODIMENT 1 | 5000 | 24.30 |
| | 1000 | 12.15 |
| | 500 | 10.75 |
| CONTROL | | 0 |

The result indicates that Embodiment 1 shows noticeable fungicidal activity.

Incorporation By Reference

References and citations to other documents, such as patents, patent applications, patent publications, journals, books, papers, web contents, have been made in this disclosure. All such documents are hereby incorporated herein by reference in their entirety for all purposes.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance which can be adapted to the practice of this invention in its various embodiments and equivalents thereof.

What is claimed is:

1. An insecticide composition comprising environmentally safe active ingredient of 8-epicedrol.

2. The insecticide composition of claim 1 further comprising one or more botanical essential oils or concretes as boosters.

3. The insecticide composition of claim 2, wherein each of the one or more botanical essential oils or concretes is selected from Camphor oil, Litsea oil, Spearmind oil, Citronella oil, Cassia oil, Star anise oil, Cedar wood oil, Peppermint oil, Wintergreen oil and Orris concrete.

4. The insecticide composition of claim 3 further comprising one or more surfactants.

5. The insecticide composition of claim 4, wherein each of the surfactants is selected from the group consisting of: ethanolamine dodecyl sulfate (K12 EA), sodium dodecyl sulfate (AS), potassium dodecyl phosphate(PK), linear sodium alkyl benzene sulfonate (LAS), sodium oleoyl amino fatty acid, sodium N-oleoyl-N-methyl taurinate, sodium salt α-sulfo fatty acid methyl ester (MES), sodium stearate, sodium oleate, ammonium oleate, potassium oleate, potassium stearate, zinc stearate, magnesium stearate, polyoxyethylene fatty alcohol sodium sulfate (AES), ethoxylated alkyl ester sulfo succinate, alkylbenzene sulfonic acid, sodium alkyl sulfonate, α-alkene-sulfonate (AOS), secondary alkane sulfonate (SAS), sodium dialkyl ester sulfonsuccinate, N-acyl glutamate (AGA), triethanolamine polyoxyethylene fatty alcohol sulfate (TA-40), sulfonated caster oil, Span-20, 40, 60, 65, 80, Tween-20, 40, 60, 65, 80, secondary alcohol polyoxyethylene ether (JFC), fatty alcohol polyoxyethylene(3) ether (AEO3), fatty alcohol polyethoxylate(7) ether (AEO7), fatty alcohol polyoxyethylene(9) ether (AEO9), fatty alcohol polyethoxylate(10) ether (AEO10), fatty alcohol Polyoxyethylene(15) ether (AEO15), fatty acid alkanol amide, fatty acid polyoxyethylene(10) ester, glyceryl oleate, glycerol trioleate, glyceryl stearate, alkylphenolpolyoxyethylene(10) ether, coco fatty diethanol amide, coco fatty monoethanol amide, caster oil polyoxyethylene ether, ethoxylatedmetluylglucosidesesquistearate (MSE), methyl glucosidesesquistearate, sucrose fatty acid ester, polyoxyethylene-polyoxypropylene glycols, polyoxyethylenealkylamide, dodecyl dimethyl betaine, alkyl dimethyl betaine, coco amino propyl betaine, carboxylate-type imidazolineampholytic surfactant, carbomer, ethoxylatedlanoilu, ethoxylatedlanoilu alcohol, lanolin fatty acid, iso-propyl lanolate, liquid lanolin, and lecithin.

6. The insecticide composition of claim 4 further comprising one or more synergists.

7. The insecticide composition of claim 6, wherein each of the one or more synergists is selected from the group consisting of: Alkyl glucoside, lactic acid, methyl silicone oil, isopropyl alcohol, ethyl lactate, ethanol, oleic acid, polyoxyethylene alkyl ether, alkyl sulfates, dialkyl succinate, alkyl amide taurine salt, fatty alcohol polyoxyethylene ether sulfonate, fatty alcohol ethoxylates, lactic acid ethyl ester, phenethyl propionate, polyglyceryl stearate, sodium polyacrylate, calcium lignin sulfonate, dialkyl succinate sulfonate, ethylene glycol monoether, amyl acetate, 2-butanone, n-butyl alcohol, and dibutyl phthalate and n-butyl acetate.

8. The insecticide composition of claim 1, wherein the composition is in the form emulsion, powder, water-based spray, aerosol, granule, powder, fumigation or lotion.

9. A method for treating an insect infestation, comprising applying an environmentally safe insecticidal composition according to claim 5.

10. A method for treating an insect infestation, comprising applying an environmentally safe insecticidal composition according to claim 7.

* * * * *